US011712717B2

(12) United States Patent
Sherrit et al.

(10) Patent No.: US 11,712,717 B2
(45) Date of Patent: Aug. 1, 2023

(54) DUAL FREQUENCY ULTRASONIC AND SONIC ACTUATOR WITH CONSTRAINED IMPACT MASS

(71) Applicant: CALIFORNIA INSTITUTE OF TECHNOLOGY, Pasadena, CA (US)

(72) Inventors: Stewart Sherrit, Pasadena, CA (US); Xiaoqi Bao, Pasadena, CA (US); Yoseph Bar-Cohen, Pasadena, CA (US); Mircea Badescu, Pasadena, CA (US); Hyeong Jae Lee, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 1124 days.

(21) Appl. No.: 16/367,075

(22) Filed: Mar. 27, 2019

(65) Prior Publication Data

US 2019/0299252 A1    Oct. 3, 2019

Related U.S. Application Data

(60) Provisional application No. 62/795,770, filed on Jan. 23, 2019, provisional application No. 62/649,144, filed on Mar. 28, 2018.

(51) Int. Cl.
*B06B 1/06* (2006.01)
*B25D 16/00* (2006.01)
(Continued)

(52) U.S. Cl.
CPC ...... *B06B 1/0614* (2013.01); *A61B 17/22012* (2013.01); *B25D 16/00* (2013.01);
(Continued)

(58) Field of Classification Search
CPC .............. A61B 17/22; A61B 17/22012; A61B 2017/22015; A61B 17/32;
(Continued)

(56) References Cited

U.S. PATENT DOCUMENTS 3,808,820 A   5/1974  Bodine
3,900,826 A   8/1975  Dowling et al.
(Continued)

FOREIGN PATENT DOCUMENTS

WO       01/83933 A1    11/2001
WO    2017/151178 A1     9/2017
(Continued)

OTHER PUBLICATIONS

Bar-Cohen, Y., et al. "Ultrasonic/Sonic Driller/Corer (USDC) with Integrated Sensors," NTR, Aug. 30, 1999, Item No. 0448b, (Nov. 17, 1999). NASA Tech Briefs, vol. 25, No. 1, Jan. 2001, pp. 38-39.
(Continued)

*Primary Examiner* — Andrew M Tecco
*Assistant Examiner* — Jacob A Smith
(74) *Attorney, Agent, or Firm* — Steinfl + Bruno LLP

(57) ABSTRACT

A dual frequency ultrasonic and sonic actuator with constrained impact mass is presented. According to one aspect, displacement of the impact mass is constrained by cavity to which ultrasonic stress from the tip of a horn is applied. According to another aspect, the displacement of the impact mass is constrained by a spring attached to the tip of the horn. According to another aspect, the displacement of the impact mass is constrained by a flexure. The constrained impact mass converts the ultrasonic stress to lower frequency sonic stress that is coupled to a transmitting element for transmission through a surface. According to one aspect, the transmitting element is a longitudinal probe. According to another aspect, the transmitting element is a drill bit used
(Continued)

to penetrate though the surface. According to another aspect, the transmitting element is a thumper used to transmit elastic waves though the surface.

17 Claims, 15 Drawing Sheets

(51) Int. Cl.
 *G01V 1/00* (2006.01)
 *A61B 17/22* (2006.01)
(52) U.S. Cl.
 CPC .... *G01V 1/006* (2013.01); *A61B 2017/22025* (2013.01); *A61B 2017/22027* (2013.01); *B06B 2201/73* (2013.01); *B25D 2250/311* (2013.01)
(58) Field of Classification Search
 CPC ........... A61B 17/320068; A61B 2017/320089; B25D 16/00
 USPC ....................... 173/90, 2, 102, 103, 104, 112
 See application file for complete search history.

(56) References Cited

U.S. PATENT DOCUMENTS

| | | | |
|---|---|---|---|
| 3,901,075 A | 8/1975 | Hampton et al. | |
| 5,549,170 A | 8/1996 | Barrow | |
| 5,595,243 A | 1/1997 | Maki et al. | |
| 5,713,848 A | 2/1998 | Dubrul et al. | |
| 5,906,623 A | 5/1999 | Peterson | |
| 5,971,949 A | 10/1999 | Levin et al. | |
| 5,984,023 A | 11/1999 | Sharma et al. | |
| 6,551,337 B1 | 4/2003 | Rabiner et al. | |
| 6,617,760 B1 | 9/2003 | Peterson et al. | |
| 6,863,136 B2 | 3/2005 | Bar-Cohen et al. | |
| 7,156,189 B1* | 1/2007 | Bar-Cohen | A63B 29/08 173/112 |
| 7,740,088 B1* | 6/2010 | Bar-Cohen | E21B 6/08 310/323.19 |
| 8,657,027 B2 | 2/2014 | Sherrit et al. | |
| 8,958,270 B2 | 2/2015 | Sherrit et al. | |
| 10,349,972 B2 | 7/2019 | Bar-Cohen et al. | |
| 2002/0077643 A1 | 6/2002 | Rabiner et al. | |
| 2002/0107446 A1 | 8/2002 | Rabiner et al. | |
| 2002/0168611 A1 | 11/2002 | Kim et al. | |
| 2003/0099917 A1 | 5/2003 | Wietecha et al. | |
| 2003/0157458 A1 | 8/2003 | Buchanan et al. | |
| 2003/0181812 A1 | 9/2003 | Rabiner et al. | |
| 2004/0097996 A1 | 5/2004 | Rabiner et al. | |
| 2004/0147945 A1 | 7/2004 | Fritzsch et al. | |
| 2904/0127925 | 7/2004 | Du et al. | |
| 2005/0209620 A1* | 9/2005 | Du | A61B 17/32053 606/167 |
| 2006/0184186 A1 | 8/2006 | Noone | |
| 2007/0193757 A1 | 8/2007 | Bar-Cohen et al. | |
| 2008/0281253 A1 | 11/2008 | Injev et al. | |
| 2008/0306499 A1 | 12/2008 | Katoh et al. | |
| 2009/0069712 A1 | 3/2009 | Mulvihill et al. | |
| 2009/0270888 A1 | 10/2009 | Patel et al. | |
| 2010/0174233 A1 | 7/2010 | Kuban et al. | |
| 2010/0204613 A1 | 8/2010 | Rollins et al. | |
| 2011/0056713 A1 | 3/2011 | Sherrit et al. | |
| 2011/0094765 A1 | 4/2011 | Aldrich et al. | |
| 2011/0208222 A1 | 8/2011 | Ljahnicky et al. | |
| 2012/0014221 A1* | 1/2012 | Sherrit | B23K 20/10 264/485 |
| 2912/0014221 | 1/2012 | Sherrit et al. | |
| 2012/0037390 A1 | 2/2012 | Bao et al. | |
| 2012/0209303 A1 | 8/2012 | Frankhouser | |
| 2014/0107683 A1 | 4/2014 | Kühner et al. | |
| 2014/0249472 A1 | 9/2014 | Mulvihill et al. | |
| 2014/0371636 A1* | 12/2014 | Bond | A61B 17/22012 601/2 |
| 2015/0351644 A1 | 12/2015 | Lee et al. | |
| 2016/0038165 A1 | 2/2016 | Cook et al. | |
| 2016/0128769 A1 | 5/2016 | Rontal et al. | |
| 2016/0346519 A1 | 12/2016 | Bagwell et al. | |
| 2017/0252058 A1 | 9/2017 | Bar-Cohen et al. | |
| 2018/0185052 A1 | 7/2018 | Zhou et al. | |

FOREIGN PATENT DOCUMENTS

| | | |
|---|---|---|
| WO | 2017/192539 A1 | 11/2017 |
| WO | 2019/191330 A1 | 10/2019 |

OTHER PUBLICATIONS

Final Office Action for U.S. Appl. No. 15/218,979, filed Jul. 25, 2016 on behalf of California Institute of Technology. dated Jan. 28, 2019. 21 pages.
International Preliminary Report on Patentability for International Application No. PCT/US2016/043908 filed Jul. 25, 2016 on behalf of California Institute of Technology. dated Sep. 4, 2016. 14 pages.
International Search Report and Written Opinion for International application No. PCT/US2016/043908 filed Jul. 25, 2016 on behalf of California Institute of Technology. dated Nov. 21, 2016. (19 pages).
International Search Report for International Application PCT/US2019/024429 filed on Mar. 27, 2019 on behalf of California Institute of Technology dated Jul. 10, 2019. 4 pages.
Lee et al., "Dual-Frequency Elastic Wave Transmitter and Receiver (DFETR) array." CIT 8179-P, (2009) 6 pages.
Non-Final Office Action for U.S. Appl. No. 15/218,979, filed Jul. 25, 2016 on behalf of California Institute of Technology. dated Oct. 18, 2018. 24 pages.
Notice of Allowance for U.S. Appl. No. 15/218,979, filed Jul. 25, 2016, on behalf of California Institute of Technology. dated May 8, 2019. 9 pages.
Sherrit et al., "Ultrasonic horn with constrained impact mass and fixed probes" CIT 6864-P5. (2018). 8 pages.
Sherrit, S., et al. "Miniature Low-Mass Drill Actuated by Flextensional Piezo Stack", NASA Tech Briefs, vol. 34, No. 8, Aug. 2010, pp. 6-7.
Written Opinion for International Application PCT/US2019/024429 filed on Mar. 27, 2019 on behalf of California Institute of Technology. dated Jul. 10, 2019. 9 pages.

* cited by examiner

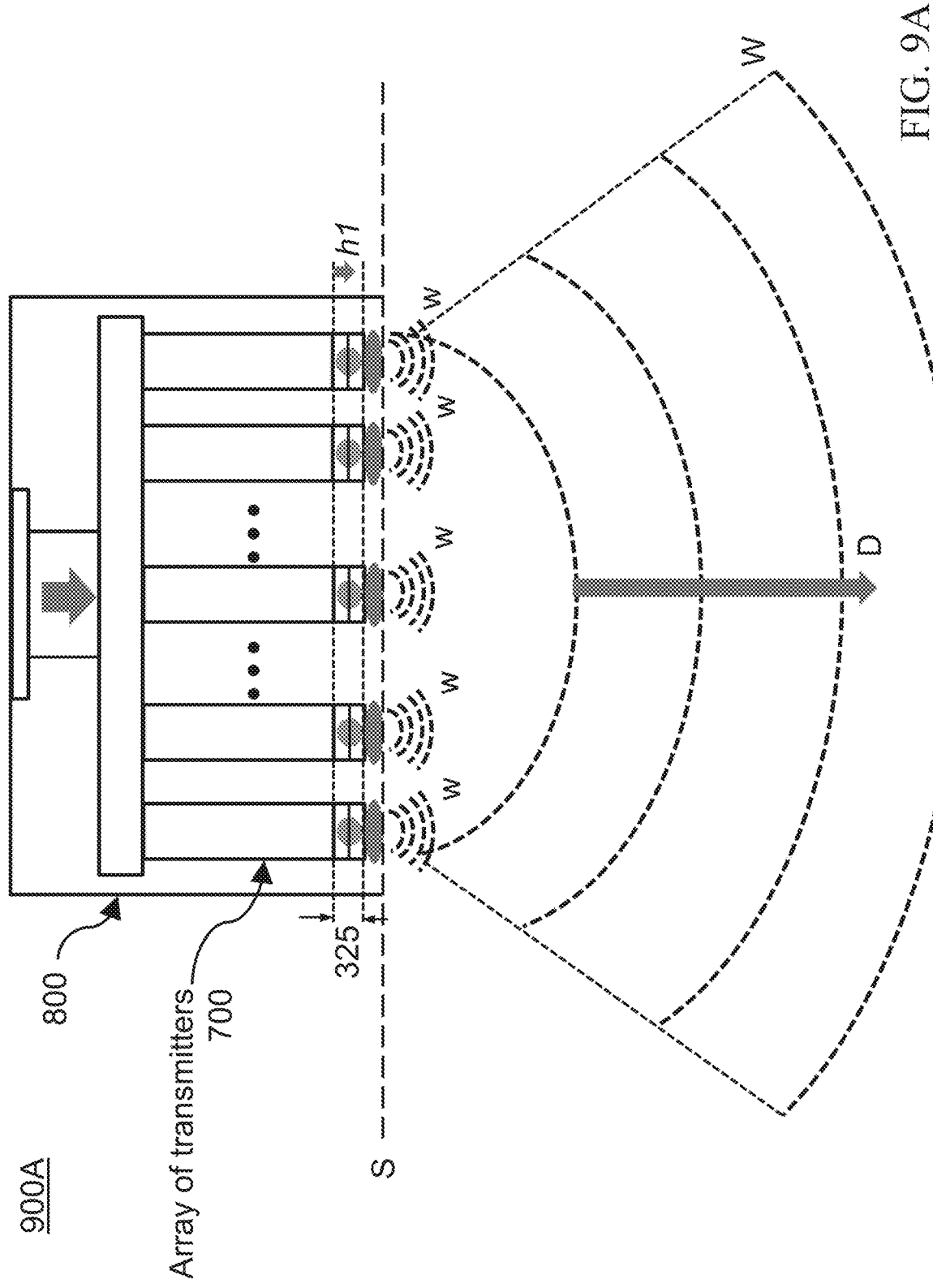

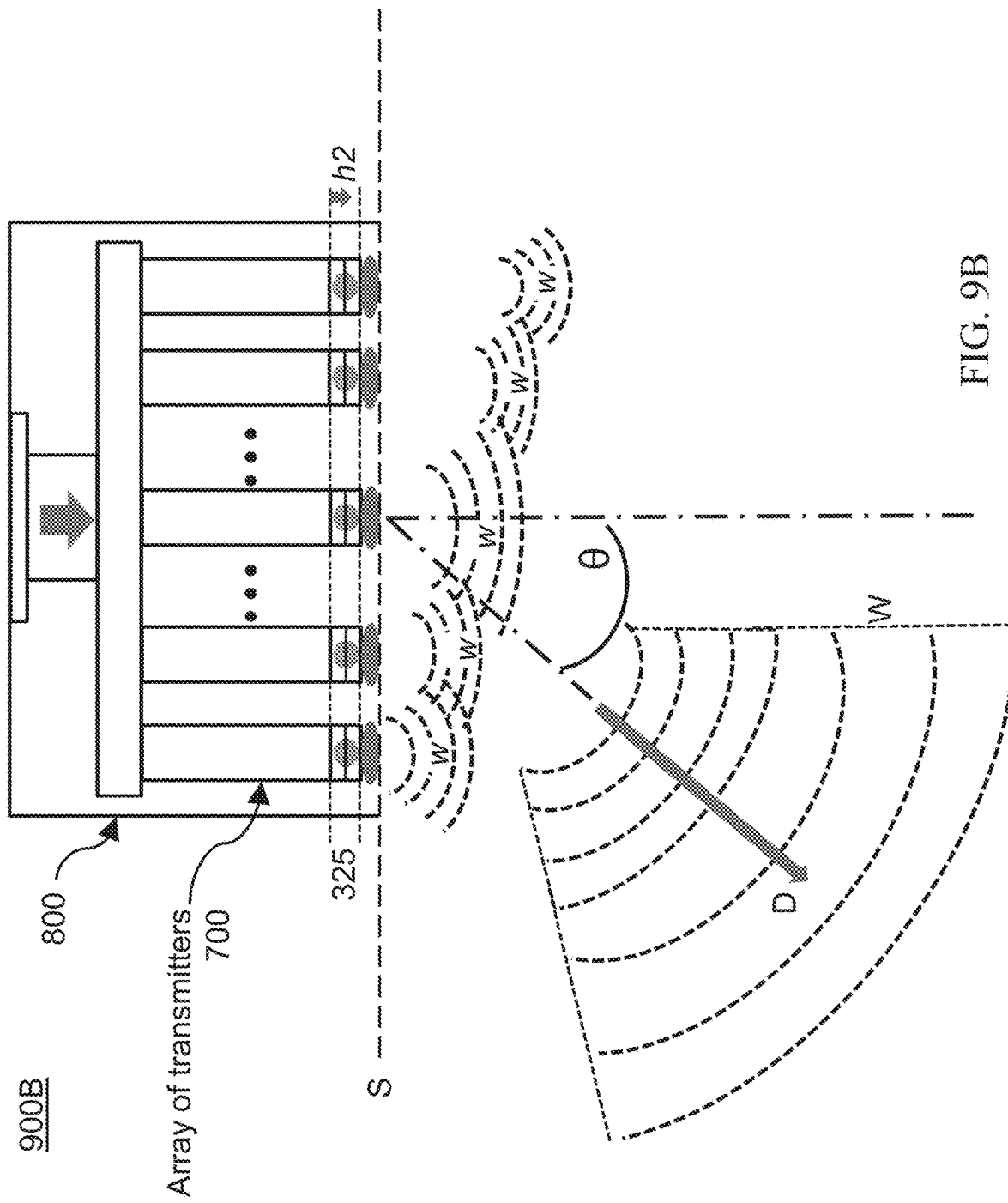

DUAL FREQUENCY ULTRASONIC AND SONIC ACTUATOR WITH CONSTRAINED IMPACT MASS

CROSS REFERENCE TO RELATED APPLICATIONS

The present application claims priority to and the benefit of U.S. provisional patent application Ser. No. 62/649,144 entitled "Ultrasonic Horn with Constrained Impact Mass and Fixed Probes", filed on Mar. 28, 2018, the disclosure of which is incorporated herein by reference in its entirety.

The present application also claims priority to and the benefit of U.S. provisional patent application Ser. No. 62/795,770 entitled "Dual-Frequency Elastic Wave Transmitter and Receiver (Dfetr) Array", filed on Jan. 23, 2019, the disclosure of which is incorporated herein by reference in its entirety.

The present application may be related to U.S. Pat. No. 6,863,136 B2 entitled "Smart Ultrasonic/Sonic Driller/Corer" issued on Mar. 8, 2005, the disclosure of which is incorporated herein by reference in its entirety. The present application may also be related to U.S. Pat. No. 6,617,760 B1 entitled "Ultrasonic Resonator" issued on Sep. 9, 2003, the disclosure of which is incorporated herein by reference in its entirety.

STATEMENT OF GOVERNMENT GRANT

The invention described herein was made in the performance of work under a NASA contract NNN12AA01C, and is subject to the provisions of Public Law 96-517 (35 USC 202) in which the Contractor has elected to retain title.

TECHNICAL FIELD

The present disclosure relates to systems and methods for generating dual ultrasonic and sonic stress on a surface for transmission into a medium. Applications may include drilling, coring, probing, testing and penetrating of the medium.

BACKGROUND

FIG. 1 shows a drilling device (100) that includes an ultrasonic/sonic actuator (101) that generates ultrasonic and sonic stresses that is coupled to a base (110b) of a probe (110) which acts as a transmitting element. The ultrasonic and sonic stresses are transmitted via the probe (110) to a surface S that is in contact with a tip (110a) of the probe (110). The ultrasonic/sonic actuator (101) includes an ultrasonic actuator (102) coupled, via a horn (130) of the ultrasonic actuator (102), to a sonic actuator (105). The base of the horn (130) is fixed to a mounting nodal plane (135) which defines a plane where no axial displacement of the horn (130) exists. As described in the above referenced U.S. Pat. No. 6,863,136 B2, the disclosure of which is incorporated herein by reference in its entirety, the ultrasonic actuator (102) couples ultrasonic stress (e.g., displacement, vibration) generated by a combination of piezoelectric elements (140) compressed by action of a bolt (150) against a backing structure (160), to the horn (130). In turn, the horn (130) couples an amplified version of the ultrasonic stress to the sonic actuator (105) which translates/converts the amplified ultrasonic stress to a sonic stress. Accordingly, sonic and ultrasonic stresses are coupled to the probe (110) for a corresponding displacement at the tip (110a) of the probe (110) in contact with the surface S.

As described in the above referenced U.S. Pat. No. 6,863,136 B2, the disclosure of which is incorporated herein by reference in its entirety, a prior art sonic actuator (105) may be based on a coupling of the ultrasonic stress from the horn (130) to an impact mass, also referred to as a striker, (120), whose displacement is not constrained (e.g., free mass). FIG. 2A shows that the impact mass (120) according to said referenced US patent is free to travel under actuation (impact) by the horn (130) in an axial (i.e., longitudinal) direction of the probe (110), between a tip (131) of the horn (130) and the base (110b) of the probe (110) which in combination define a displacement of the impact mass (120). Bouncing of the impact mass (120) back and forth against the tip (131) of the horn (130) and the base (110b) in turn generates sonic stress that is coupled to the probe (110). The probe (110) is not rigidly coupled (i.e., not fixed) to the horn (130), rather slide-ably coupled via an extension (132) that slides within a groove (126) formed in the horn (130), in other words, the probe (110) (e.g., a surface of the probe impacted by the mass) is not at a fixed distance from the horn (130). Therefore, the displacement of the impact mass (120) may vary according to a distance between the base (110b) of the probe (110) and the tip (131) of the horn (130). Such displacement may vary, for example, from smaller displacement shown in FIG. 2A for a distance (225a) between the base (110b) of the probe (110) and the tip (131) of the horn (130), to a larger displacement shown in FIG. 2B for a distance (225b) between the base (110b) of the probe (110) and the tip (131) of the horn (130), and up to a maximum displacement that may be defined, for example, by a length (225m) of the extension (132). More description of the slidable coupling, also known as a "floating attachment", between the probe (110), via the rigidly coupled extension (132) to the probe (110), and the horn (130), can be found in the above referenced U.S. Pat. No. 6,617,760 B1, the disclosure of which is incorporated herein by reference in its entirety.

With continued reference to FIG. 2A and FIG. 2B, as can be clearly understood by a person skilled in the art, the varying displacement of the impact mass (120) due to the floating attachment of the probe (110) to the horn (130), which does not provide a fix distance between the probe (110) and the horn (130), causes a varying sonic frequency of a stress induced by the impact mass (120). Such varying sonic frequency stress is coupled to the probe (110) and ultimately coupled to the surface S of FIG. 1. Furthermore, the floating attachment of the probe (110) to the horn (130) causes a loss in energy transferred from a tip (131) of the horn (130) to the tip (110a) of the probe (110) since only a portion of the energy is axially (longitudinally) coupled to the probe (110), as another portion of the energy is transferred via transverse coupling to the probe (110) to create lateral motion of the probe (110) (e.g., for cleaning of the probe as described in U.S. Pat. No. 6,617,760 B1). Accordingly, the floating attachment causes a reduced axial displacement at the tip (110a) of the probe (110) at a frequency that is lower (e.g., subharmonic) than an ultrasonic frequency of vibrations at a tip of the horn (130).

Based on the above, the prior art ultrasonic/sonic actuator described with reference to FIG. 2A and FIG. 2B may not allow application of a stress at the surface S of FIG. 1 having a substantially fixed ultrasonic or sonic frequency. Due to the floating attachment used to couple the horn (130) to the probe (110), efficiency in energy transfer to the probe (130) is reduced and therefore a lower amplitude displacement is provided at the tip (110a) of the probe (110). Teachings according to the present disclosure describe an ultrasonic/ sonic actuator that can be used to efficiently apply a stress at the surface S having a substantially fixed and controllable ultrasonic and/or sonic frequencies.

SUMMARY

According to one embodiment the present disclosure, a dual frequency actuator is presented, the dual frequency actuator comprising: an ultrasonic actuator comprising a horn coupled to a source of ultrasonic frequency vibrations, the horn configured to amplify the ultrasonic frequency vibrations along an axial direction of the horn; a transmitting element at a fixed distance from the horn; and an impact mass disposed between the horn and the transmitting element, a displacement of the impact mass being constrained into the axial direction, wherein the impact mass is configured to strike the transmitting element in response to the ultrasonic frequency vibrations to produce sonic impacts at the transmitting element.

According to a second embodiment of the present disclosure, a method for generation of dual ultrasonic and sonic frequency impacts is presented, the method comprising: coupling ultrasonic frequency vibrations to a horn for amplifying the ultrasonic frequency vibrations along an axial direction of the horn; arranging a transmitting element at a fixed distance from the horn; arranging an impact mass between the horn and the transmitting element, a displacement of the impact mass being constrained into the axial direction; and striking, via the impact mass, the transmitting element in response to the ultrasonic frequency vibrations to produce sonic impacts at the transmitting element.

Further aspects of the disclosure are shown in the specification, drawings and claims of the present application.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure. Same reference designators refer to same features.

FIG. 9A shows a configuration according to an embodiment of the present disclosure of the transmitter assembly of FIG. 8 for transmitting sonic waves through a surface in contact with transmitting thumpers of the array.

FIG. 9B shows a configuration according to an embodiment of the present disclosure of the transmitter assembly of FIG. 8 for transmitting and steering ultrasonic waves through a surface in contact with transmitting thumpers of the array.

DETAILED DESCRIPTION

Figure 1:
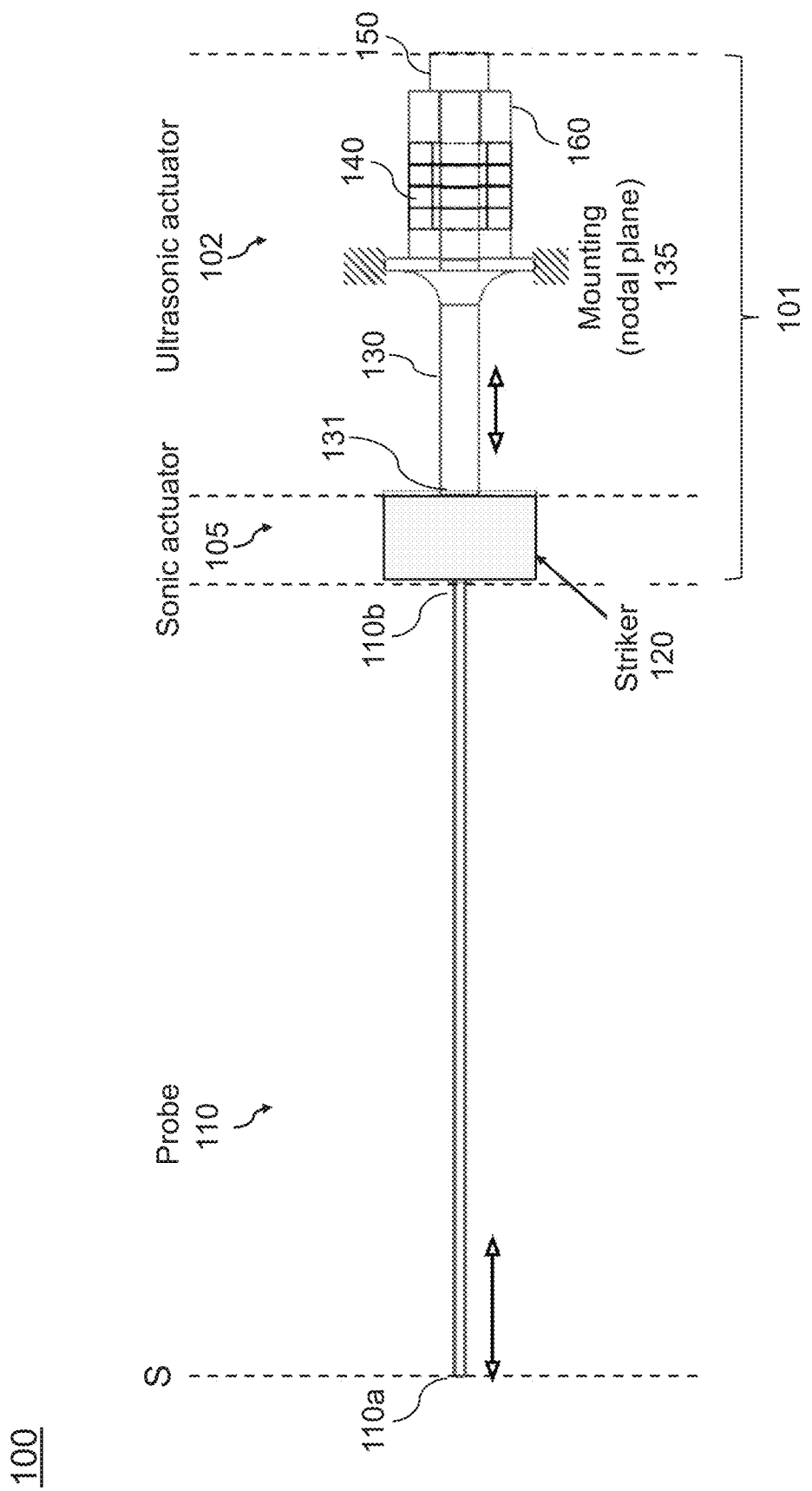
FIG. 1 shows a dual frequency ultrasonic and sonic actuator used in a drilling device.
Figure 2A:
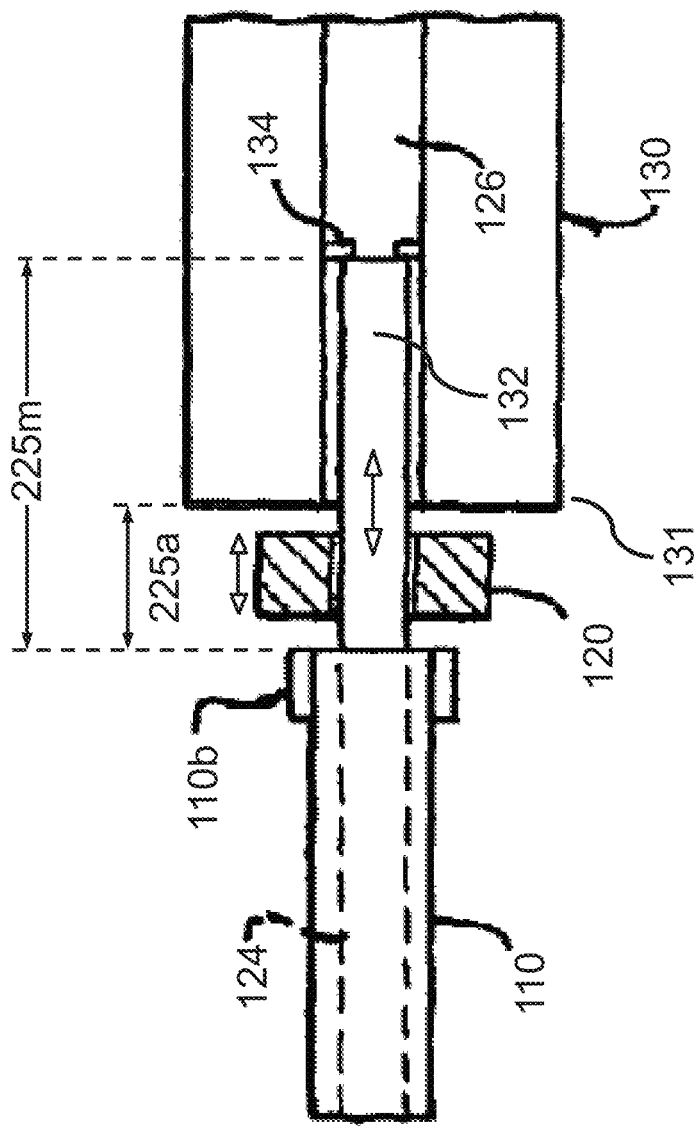
FIG. 2A and FIG. 2B show a prior art implementation of a dual frequency ultrasonic and sonic actuator using an impact mass whose displacement is not constrained.
Figure 2B:
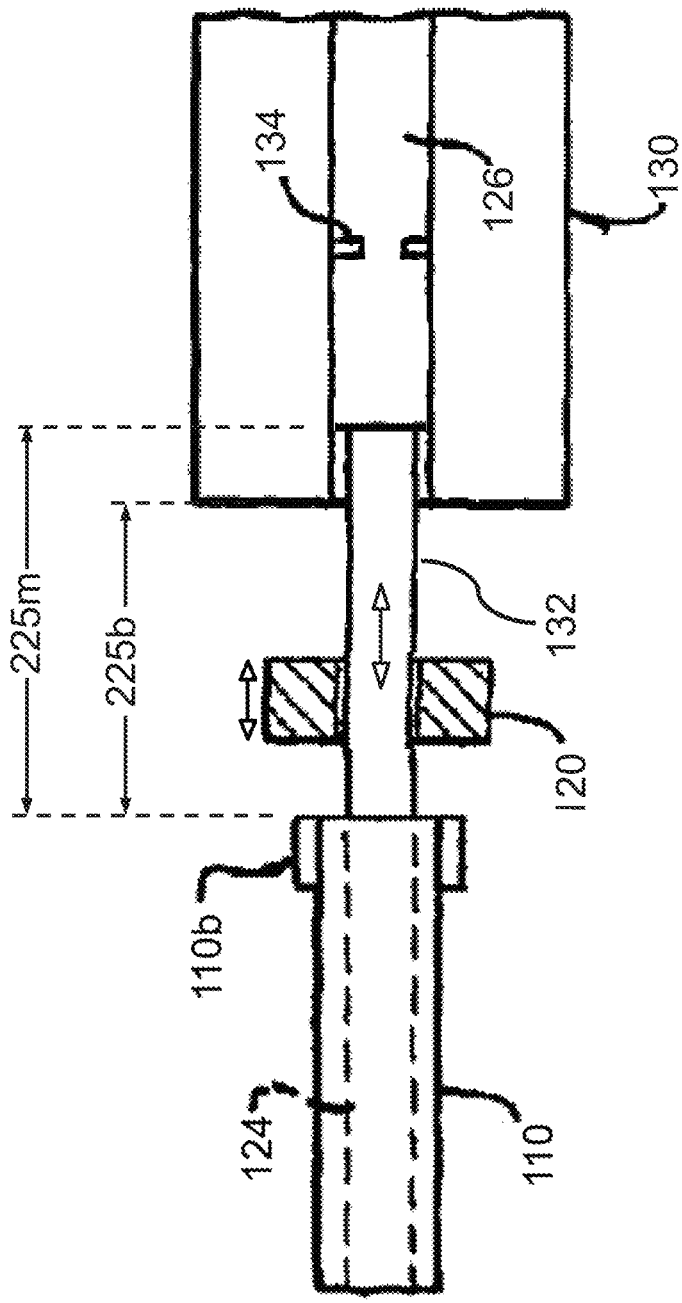

The dual frequency ultrasonic (20 KHz-40 KHz) and sonic (20 Hz-20 KHz) actuator according to the present teachings uses an axial coupling between a corresponding ultrasonic actuator and a transmitting element (e.g., probe) so to provide stress (impact) pulses at resonance ultrasonic frequency and sonic frequency to a surface in contact with the transmitting element. Furthermore, the ultrasonic actuator couples ultrasonic stress to a sonic actuator comprising an impact mass whose displacement is constrained into the axial direction so to convert the ultrasonic stress to a sonic stress. In turn, the sonic actuator couples the sonic stress to the transmitting element for provision of large sonic stress pulses to the contact surface. For example, in a case where the transmitting element is a probe, the contact surface is fractured, and in a case where the transmitting element is a thumper, an elastic wave is transmitted through the contact surface.

Because of the axial coupling and control over the ultrasonic and sonic frequencies of the stress pulses to the contact surface provided by the dual frequency ultrasonic and sonic actuator according to the present teachings, more efficient and deterministic operation of the transmitting element can be provided. For example, if the transmitting element is a drill bit, then larger impact pulses can be provided at the contact surface for more efficient drilling since all the energy is coupled axially (none, or substantially none, is coupled transversely). If the transmitting element is a thumper for generating elastic waves through the contact surface, then the elastic waves may be tuned in frequency for analysis/detection purposes or can be used in combination with a plurality of similar transmitting elements to generate elastic wave beams at controlled angles (i.e., beam steering) from the surface.

According to an embodiment of the present disclosure, the impact mass may be positioned between the transmitting element and a horn tip that can be driven to produce ultrasonic stress, wherein the distance between the horn tip and a striking surface of the transmitting element is fixed, thereby constraining the displacement of the impact mass.

According to an embodiment of the present disclosure, the impact mass may be constrained via a cavity formed inside a horn tip that can be driven to produce ultrasonic stress. The constrained impact mass may convert the ultrasonic stress into lower frequency sonic stress. Resulting impact stress pulses at ultrasonic and sonic frequencies may be coupled to the contact surface via the transmitting element.

According to another embodiment of the present disclosure, the impact mass may be constrained by a coupling to a spring coupled to the horn tip, causing the impact mass to vibrate at a lower frequency than a frequency of the horn tip. According to an exemplary embodiment of the present disclosure, the spring may be formed (integrated) in the horn tip. According to another exemplary embodiment, the impact mass may be formed at a tip of the spring.

According to another embodiment of the present disclosure, the impact mass may be constrained by a flexure. According to an exemplary embodiment of the present disclosure, the flexure has a shape of a diaphragm with a flexure membrane and supporting wall for attachment of the impact mass.

According to various embodiments of the present disclosure, the transmitting element (e.g., probe) may be either rigidly or flexibly coupled to the dual frequency ultrasonic/sonic actuator of the present teachings for transmission of axial energy (e.g., stress in the longitudinal direction of the horn). According to an exemplary embodiment, the sonic actuator may be coupled rigidly to the transmitting element for transmission of axial energy. According to another exemplary embodiment, the sonic actuator may be coupled flexibly to the transmitting element for transmission of axial energy.

Figure 3A:
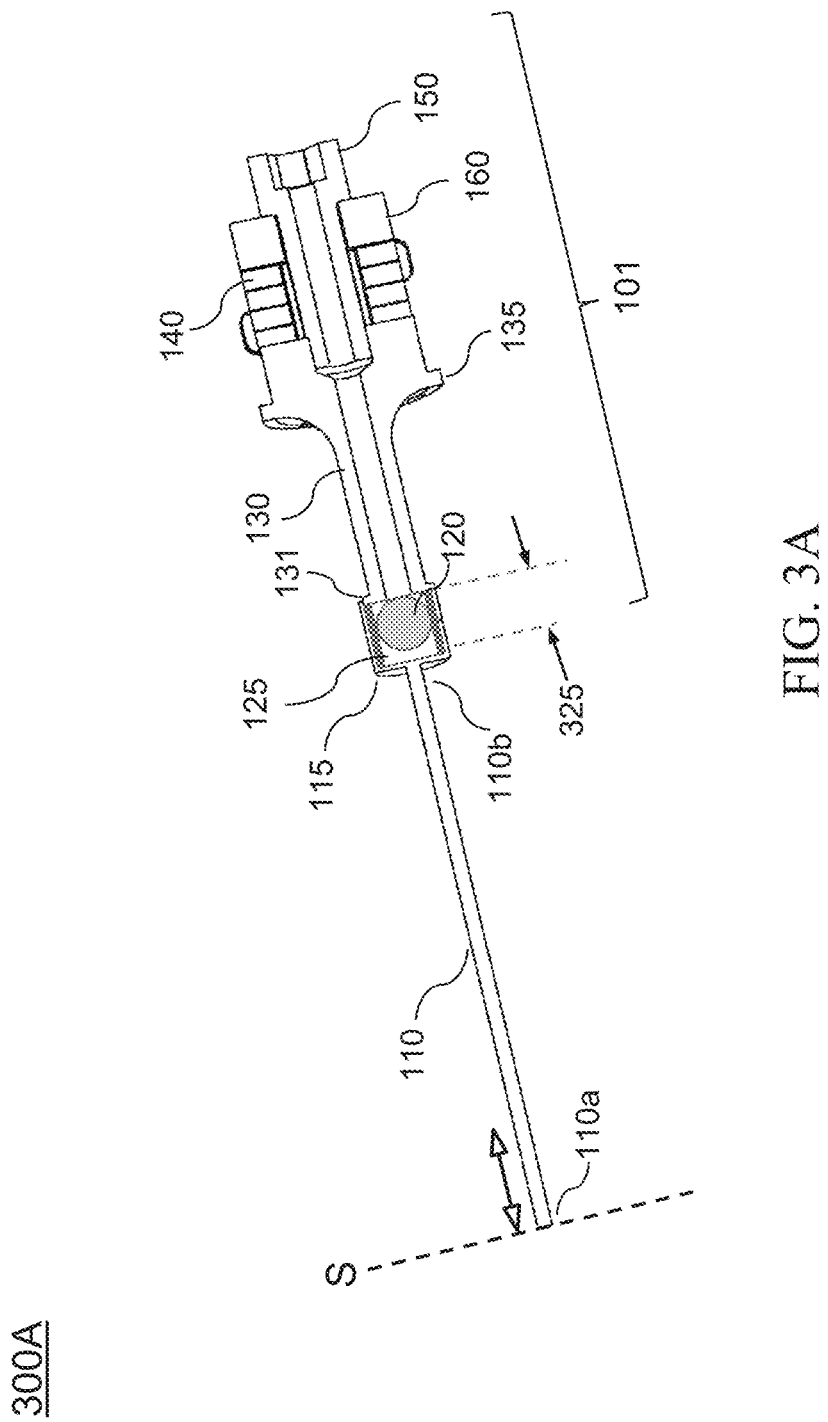
FIG. 3A and FIG. 3B show cross sectional views of an embodiment according to the present disclosure of a dual frequency ultrasonic and sonic actuator using an impact mass whose displacement is constrained by a cavity.

FIG. 3A shows a cross sectional view of an embodiment according to the present disclosure of a dual frequency ultrasonic/sonic actuator (300A) using an impact mass (120) whose displacement is constrained into an axial direction by a (rigid) cavity (125). The ultrasonic/sonic actuator (300A) includes a horn (130) that is driven by a piezoelectric stack (140) and is rigidly coupled to a probe (110). As known to a person skilled in the art, design parameters of the horn (130) can provide a resonance frequency of the horn (130) to be same as a resonance (ultrasonic) frequency of the piezoelectric stack or a (ultrasonic) subharmonic of it. Accordingly, the tip (131) of the horn (130) may apply stress at resonance or subharmonics of the piezoelectric stack (140) to the probe (130). In turn, the probe (130) transmits corresponding high frequency ultrasonic vibrations impacts (stress) from the tip (131) of the horn (130) to the contact surface S. It should be noted that since the horn (130) is rigidly coupled (fixed) to the probe (110), a distance (325) between a tip (131) of the horn (130) and a base (110b) of the probe (110) is fixed (constant).

It should be noted that the piezoelectric stack (140) shown in FIG. 3A may comprise a plurality of thin alternately poled piezoelectric layers (e.g., disks) connected mechanically in series and electrically in parallel so to provide an amplification of displacement. As it is well known to a person skilled in the art, the total displacement of a stack is proportional to the number of layers for a given applied voltage.

With continued reference to FIG. 3A, an impact mass (120) may be confined in a cavity (125) between a tip (131) of the horn (130) and the fixed probe (110). The cavity (125) is designed to allow only an axial (longitudinal) displacement of the impact mass (120) to an extent that is limited by the distance (325). In other words, under stress coupled to the impact mass (120) via the tip (131) of the horn (130), the impact mass (120) strikes a surface of the transmitting element, in this case a surface of the base (110b) of the probe (110), that is at a fixed distance (325) from the tip (131) of the horn (130). Accordingly, the impact mass (120) converts high frequency ultrasonic vibration impacts (stress) from the tip (131) of the horn (130) into low frequency sonic impacts that are transmitted (axially) by the probe (110) to the surface S.

With further reference to FIG. 3A, according to an exemplary embodiment of the present disclosure, the cavity (125) may be formed inside a tip (131) of the horn (130) via an extension (115) of the tip (131). According to another exemplary embodiment, the cavity (125) may be formed outside the tip (131) of the horn (130) within an enclosure (115) that is rigidly coupled (fixed) to the tip (131) of the horn (130). According to yet another exemplary embodiment, the cavity (125) may be formed as an extension (115) of the base (110b) of the probe (110) and rigidly coupled (fixed) to the tip (131) of the horn (130). It should be noted that the impact mass according to the present teachings may have a round shape (e.g., spherical) as shown in the figures of the present application, however such shape may not be construed as limiting the scope of the present disclosure, as applicant believes that other shapes are possible, so long the cavity is designed to constrain a displacement of the impact mass into an axial direction. Furthermore, it should be noted that the present teachings are not limited to use of a single impact mass as more than one such mass may be used, for example, within a same cavity or different cavities stacked upon one another.

Figure 3B:
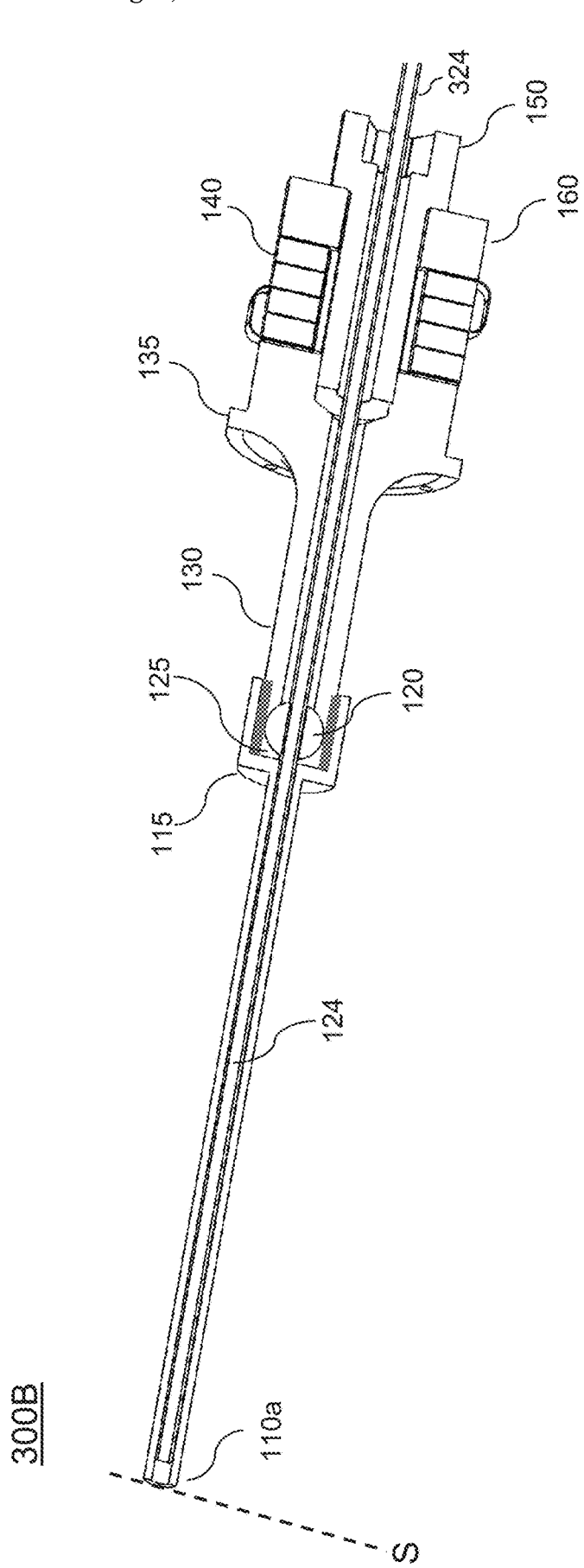

With reference to FIG. 3B, according to an embodiment of the present disclosure, the dual frequency ultrasonic/sonic actuator (300A) may comprise a bore (124) that forms a hollow core along the axial direction of the actuator (300A) to allow for insertion of a tube (324) for passage of gases, fluids and solid particles between the probe tip (110a) and the base of the actuator (300A). Such configuration may be used in applications where the probe (110) is a drill bit used for efficient drilling or in surgical tools where there may be a need to produce a hammering action or low frequency large stroke tip displacements that can break a material being probed/penetrated or investigated at the surface S.

With continued reference to FIG. 3B, according to an embodiment of the present disclosure, the tube (324) may act as an alignment/guide to guide a motion of the impact mass (120) or multiple impact masses (120) in the axial direction. Accordingly, the bore (124) passes through the impact mass(es) (120) to further constrain the masses into an axial displacement (i.e., longitudinal direction of the horn 130) only.

Figure 3C:
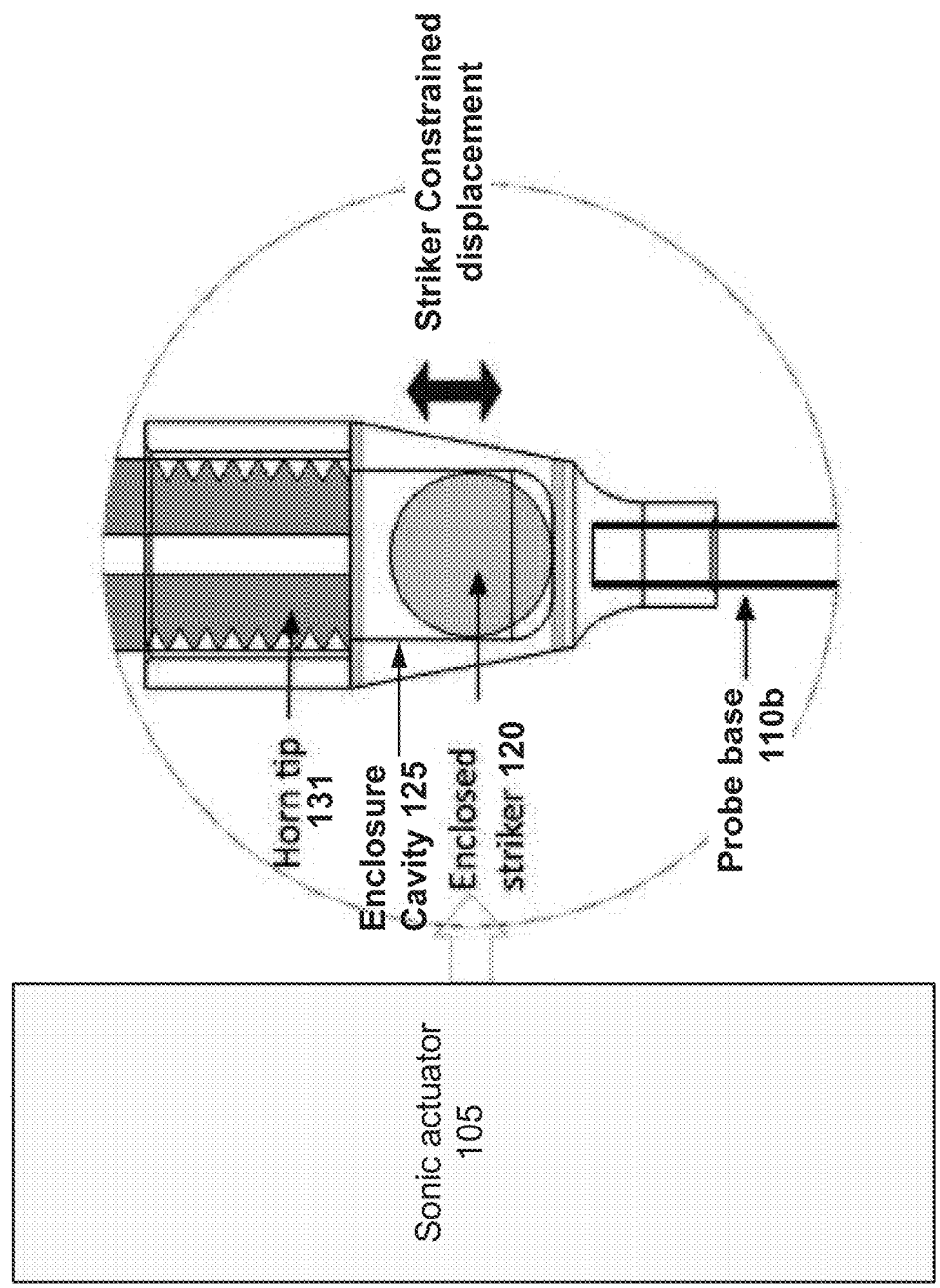
FIG. 3C shows further details of an exemplary cavity used to constrain displacement of the impact mass.

FIG. 3C shows further details of an exemplary cavity (125) used to constrain displacement of the impact mass (120) into the axial direction. The exemplary cavity (125) shown in FIG. 3C is formed by a cup-shaped enclosure with internal dimensions to only allow an axial (longitudinal) displacement of the impact mass (enclosed striker 120). As shown in FIG. 3A, the exemplary cup-shaped enclosure forming the cavity (125) is rigidly coupled on one side to the tip (132) of the horn (130), and on the other side to the base (110b) of the probe (110).

Figure 4:
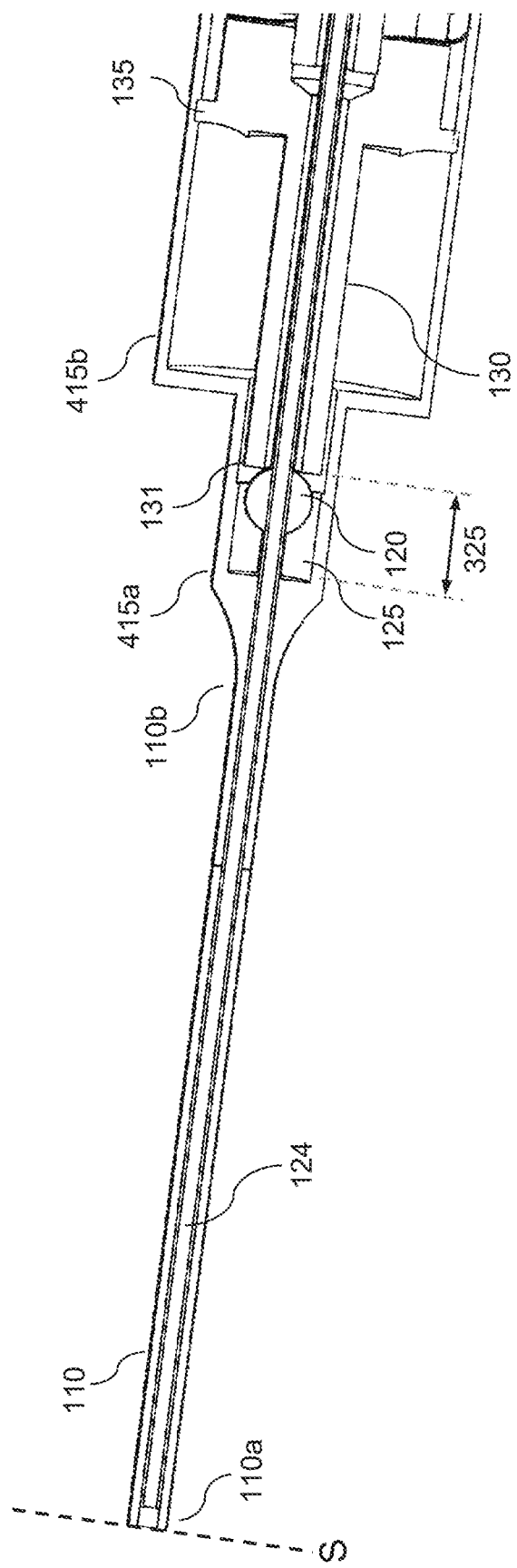
FIG. 4 shows a cross sectional view of an embodiment according to the present disclosure of a sonic actuator using an impact mass whose displacement is constrained by a cavity.

FIG. 4 shows a cross sectional view of an embodiment according to the present disclosure of a sonic actuator (400) using an impact mass (120) whose displacement is constrained into an axial direction by a cavity (125). The sonic actuator (400) includes a horn (130) that is driven by a piezoelectric stack (140), with the probe (110) (mechanically) decoupled from the tip (131) of the horn (130) and at a fixed distance (e.g., 325). As can be seen in FIG. 4, the probe (110) is coupled via elements (415a, 415b) to the mounting nodal plane (135) where there is no axial displacement (or any displacement of the probe 130). According to an exemplary embodiment, ultrasonic stress may be coupled to the tip (110a) of the probe (110) via coupling of the stress through the bore (124) if present.

With continued reference to FIG. 4, according to an embodiment of the present disclosure, element (415a) rigidly coupled to the base (110b) of the probe (110) may form a cavity (125) that constrains axial displacement of the impact mass (120). The horn tip (131) may clear the inner walls of the cavity (125) and make direct contact with the impact mass (120). Under stress coupled to the impact mass (120) via the tip (131) of the horn (130), the impact mass (120) strikes a surface of the transmitting element, in this case a surface of element (415a) rigidly coupled to the base (110b) of the probe (110), such surface being at a fixed distance (325) from the tip (131) of the horn (130). Accordingly, the impact mass (120) converts high frequency ultrasonic vibration impacts (stress) from the horn tip (131) into low frequency sonic impacts that are transmitted by the probe (110) to the surface S. The motion of the impact mass (120) may be initiated via gravity or a low stiffness spring or flexure (not shown) that places the impact mass (120) in contact with the horn tip (131).

Figure 5A:
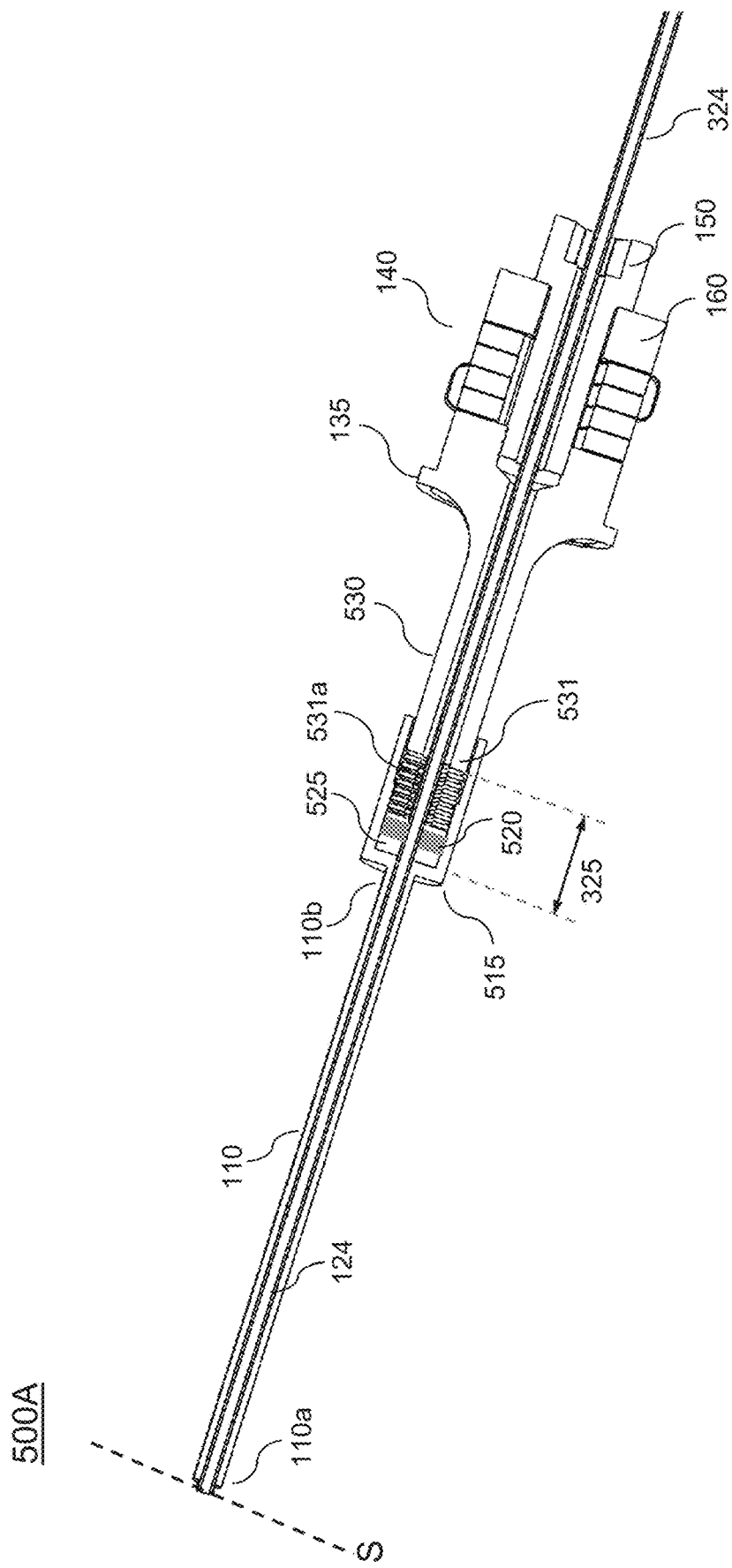
FIG. 5A shows a cross sectional view of an embodiment according to the present disclosure of a dual frequency ultrasonic and sonic actuator using an impact mass whose displacement is constrained by a spring coupled to the mass.

FIG. 5A shows a cross sectional view of an embodiment according to the present disclosure of a dual frequency ultrasonic/sonic actuator (500A) using an impact mass (520) whose displacement is constrained into an axial direction by a spring (531a) coupled to the impact mass (120). According to an exemplary embodiment, the tip (531) of the horn (530) turns into the spring (531a), in other words, the tip (531) of the horn (530) becomes the spring (531a), or the spring (531a) is formed as an extension of the tip (531) of the horn (530). In turn, the mass (520) is rigidly coupled to the spring (531).

With continued reference to FIG. 5A, according to an embodiment of the present disclosure, the probe (110) may be rigidly coupled to the horn (530) via, for example, an extension (515), so to couple ultrasonic stress from the horn (530) to the probe (110). According to an embodiment of the present disclosure, the extension (515) may form a cavity (525) for housing of the impact mass (520) and the spring (531a) while providing freedom of axial motion to the impact mass (520) and compression/extension to the spring (531a). Under stress coupled to the combination of the impact mass (520) and the spring (531a) via the tip (531) of the horn (530), the impact mass (520) strikes a surface of the transmitting element, in this case a surface of the extension (515) rigidly coupled to the base (110b) of the probe (110), that is at a fixed distance (325) from the tip (531) of the horn (530). This allows for the impact mass (520) to impact the base (110b) of the probe (110) under action of the spring (531a) coupled to the horn (530) for transmission of sonic stress to the surface S.

With further reference to FIG. 5A, according to an embodiment of the present disclosure, the horn (530) is designed to have a resonance (ultrasonic) frequency that is a harmonic (multiple) of a spring-mass resonance frequency of the combination impact mass (520) and spring (531a), where the spring-mass resonance frequency is $f_1 = (1/2\pi)(k/m)^{0.5}$, where k is the spring constant of the spring (531a) and m is the mass of the impact mass (520). Accordingly, the probe (110) and the horn (530) are driven by stress at ultrasonic frequency of the piezoelectric stack (140) and (sonic) resonance frequency, $f_1$, of the spring-mass excited by the ultrasonic frequency.

Figure 5B:
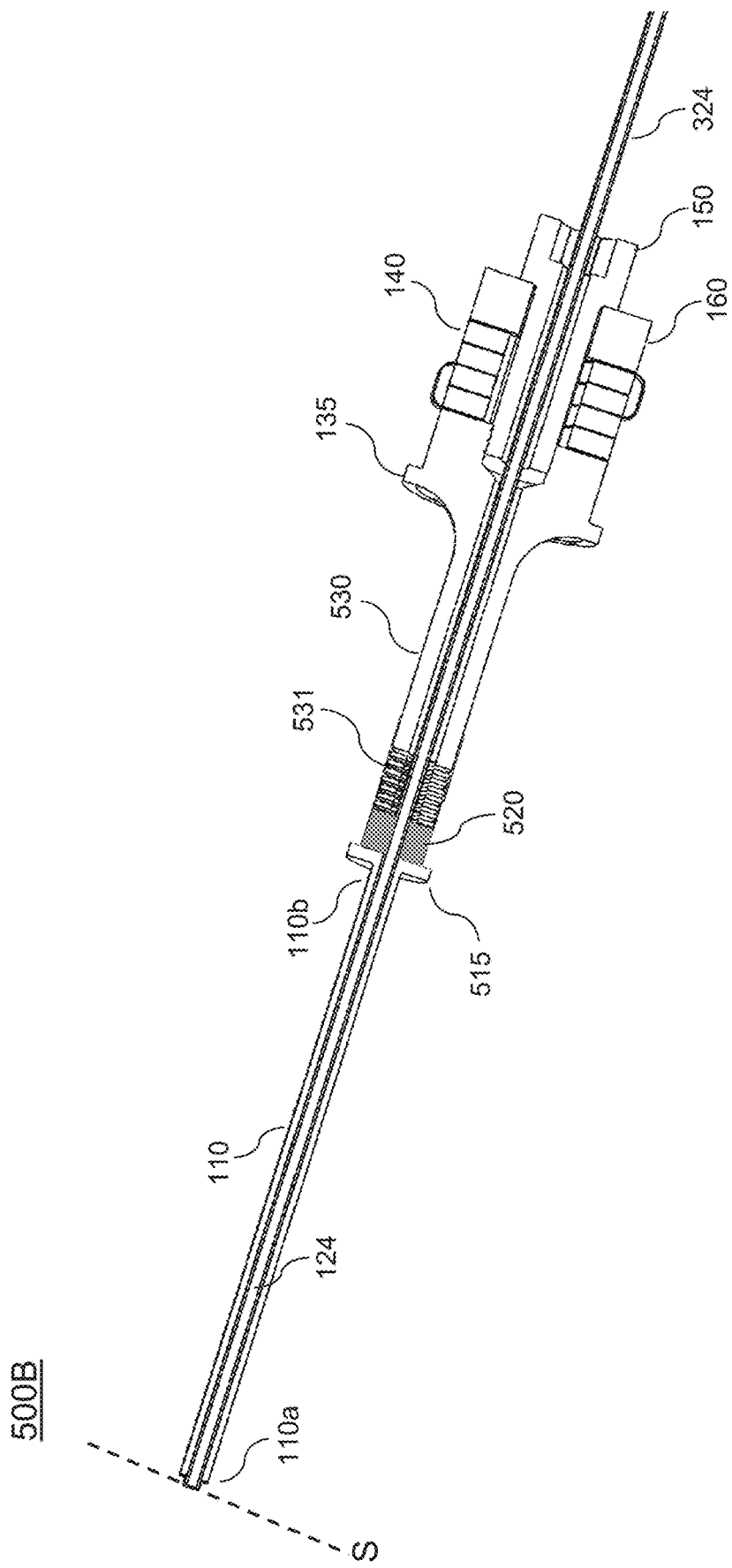
FIG. 5B shows an alternative embodiment according to the present disclosure of a dual frequency ultrasonic and sonic actuator using an impact mass whose displacement is constrained by a spring coupled to the mass.

FIG. 5B shows an alternative embodiment (500B) according to the present disclosure of a spring-mass configuration where contrary to the configuration of FIG. 5A, the probe (110) is not rigidly coupled to the horn (530), rather flexibly coupled via the combination of the mass (520) and the spring (531a). Accordingly, only lower (sonic) impact pulses at a spring-mass resonance frequency provided by the spring constant of the spring (531a) and sum of the masses of the probe (110) and the mass (520) is transmitted to the surface S in contact with the tip of the probe (110). Similar to the configuration depicted in FIG. 5A, a rigid coupling between the spring (531a) and the horn (530) allows for the ultrasonic frequency of the piezoelectric stack (140) to excite the spring-mass to resonate at the sonic frequency.

Similar to the configuration shown in FIG. 3B, the configurations shown in FIG. 5A and FIG. 5B may include a bore (124) that forms a hollow core along the axial direction of the actuator (500A, 500B) to allow for insertion of a tube (324) for passage of gases, fluids and solid particles between the probe tip (110a) and the base of the actuator. Such configuration may be used in applications where the probe (110) is a drill bit used for efficient drilling or in surgical tools where there may be a need to produce a hammering action or low frequency large stroke tip displacements that can break a material being probed/penetrated or investigated at the surface S.

Figure 6A:
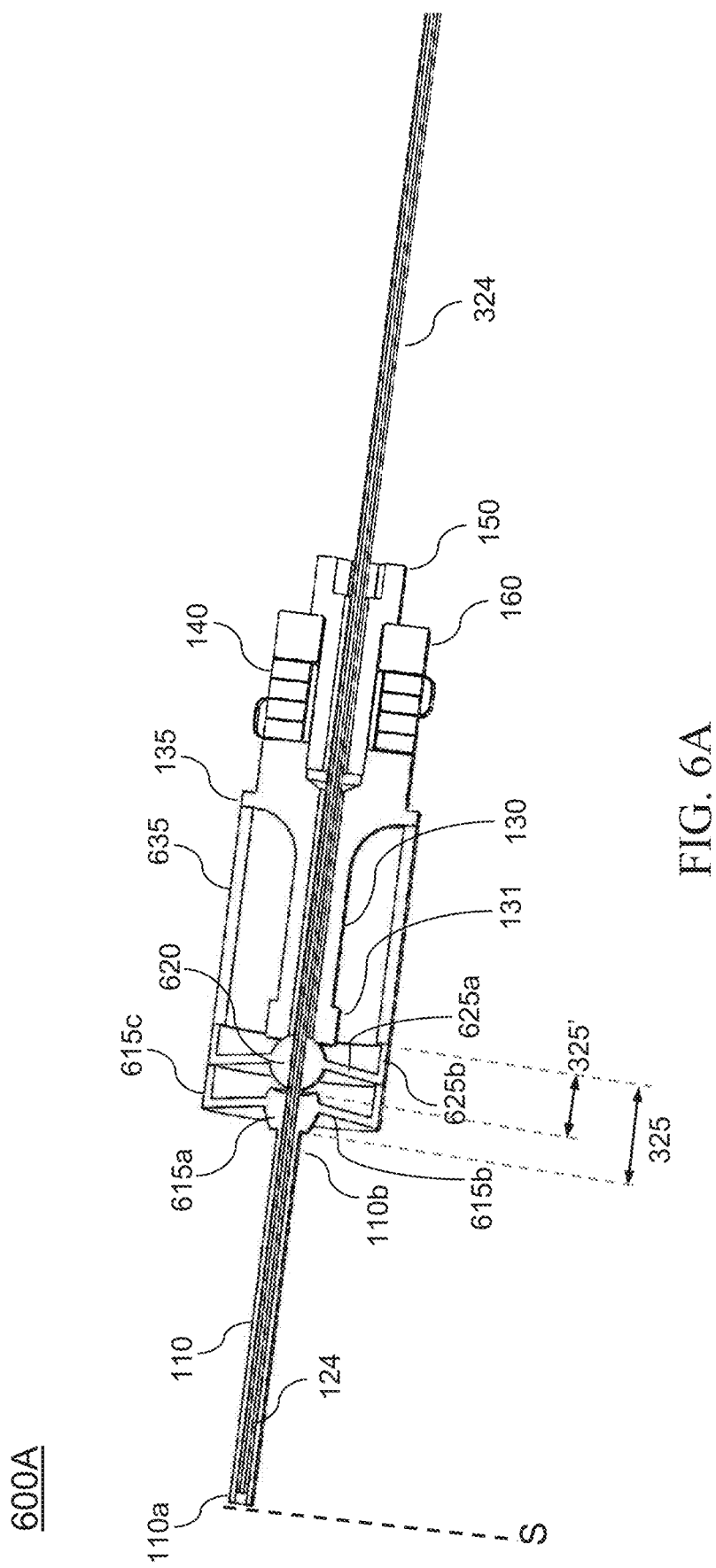
FIG. 6A shows a cross sectional view of an embodiment according to the present disclosure of a dual frequency ultrasonic and sonic actuator using an impact mass whose displacement is constrained by a flexure coupled to the mass.

FIG. 6A shows a cross sectional view of an embodiment according to the present disclosure of a dual frequency ultrasonic/sonic actuator (600A) using an impact mass (620) whose displacement is constrained into an axial direction by a flexure (625a, 625b) coupled to the impact mass (620). Furthermore, as can be seen in FIG. 6A, the probe (110a) may include a probe head (615a) that is rigidly coupled to the base (110b) of the probe (110), wherein the probe head (615a) is mounted on a flexure (615b, 615c) and is axially aligned at a (fixed) distance to the impact mass (620). Furthermore, as can be seen in FIG. 6A, the probe base (110b) and the probe head (615a) are at a respective fixed distance (325) and (325') to the tip (131) of the horn (130).

With continued reference to FIG. 6A, according to an embodiment of the present disclosure, the impact mass (620) and the probe head (615a) are coupled, via an extension (635), to the mounting nodal plane (135). It should be noted that in a practical implementation, the extension (635), or any other extension described in the present disclosure that is coupled to the nodal plane (135), may be part of a body/housing that contains the ultrasonic/sonic actuator according to the present teachings. As shown in FIG. 6A, a contact between the tip (131) of the horn (130) and the impact mass (620) causes the impact mass (620) to strike the probe head (615a) which in turn cause stress to be transmitted to the tip (110a) of the probe (110). In other words, both the probe (110) and the impact mass (620) are driven by the tip (131) of the horn (130) that operates at ultrasonic frequency provided by the piezoelectric stack (140).

With further reference to FIG. 6A, according to an embodiment of the present disclosure the impact mass (620) may be preloaded on the tip (131) of the horn (130) so that the tip (131) makes contact with the mass (620) pushing the impact mass (620) in the axial direction toward the probe head (615a), the flexure (625a, 625b) is stressed at a state away from its rest state, and a gap exists between the impact mass (620) and the probe head (615a). Accordingly, ultrasonic stress from the tip (131) of the horn (130) transmitted to the impact mass (620) builds up resonance in the flexure (625a, 625b) which causes the impact mass (620) to strike the probe head (615a) and thereby create a (sonic) stress pulse which travels to the tip (110a) of the probe (110) in contact with the surface S.

Figure 6B:
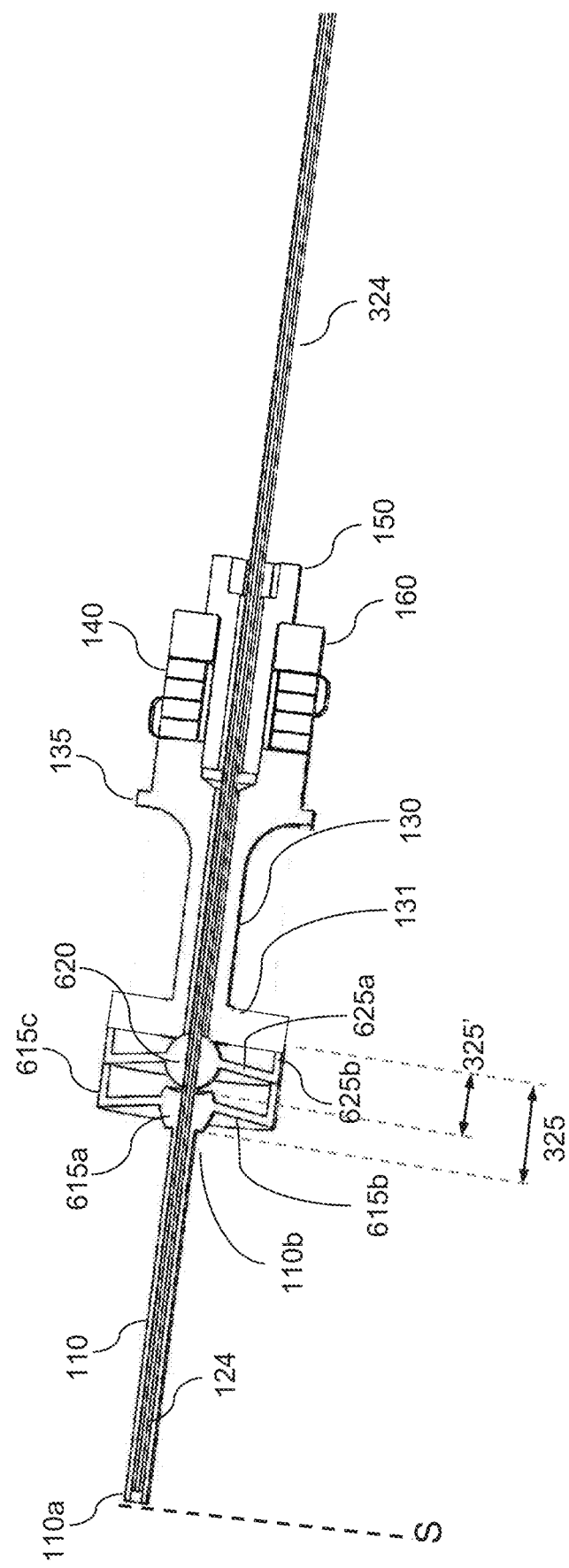
FIG. 6B shows an alternative embodiment according to the present disclosure of a dual frequency ultrasonic and sonic actuator using an impact mass whose displacement is constrained by a flexure coupled to the mass.

FIG. 6B shows an alternative embodiment (600B) according to the present disclosure of a flexure impact mass (620) configuration where contrary to the configuration of FIG. 6A, the probe head (615a) is not coupled to the mounting nodal plane (135), rather coupled to the tip (131) of the probe (130). As shown in FIG. 6B, a contact between the tip (131) of the horn (130) and the impact mass (620) causes the impact mass (620) to strike the probe head (615a) which in turn cause stress to be transmitted to the tip (110a) of the probe (110). At the same time, coupling between the tip (131) of the horn (130) and the probe head (615a) via the flexure (615b, 615c) causes ultrasonic stress to be coupled to the probe (110).

According to an exemplary embodiment, the flexures (625a, 625b) and (615b, 615c) may include, for example, a respective inner diaphragm flexure (625a, 615b) that flexes and a respective outer support wall (625b, 615c) that is coupled, in the case of FIG. 6A, to the mounting nodal plane (135) via an extension (635), and in the case of FIG. 6B, to the tip (131) of the horn (130). Furthermore, similar to other configurations described above, the configurations shown in FIG. 6A and FIG. 6B may include a bore (124) that forms a hollow core along the axial direction of the actuator (600A, 600B) to allow for insertion of a tube (324) for passage of gases, fluids and solid particles between the probe tip (110a) and the base of the actuator.

Figure 7:
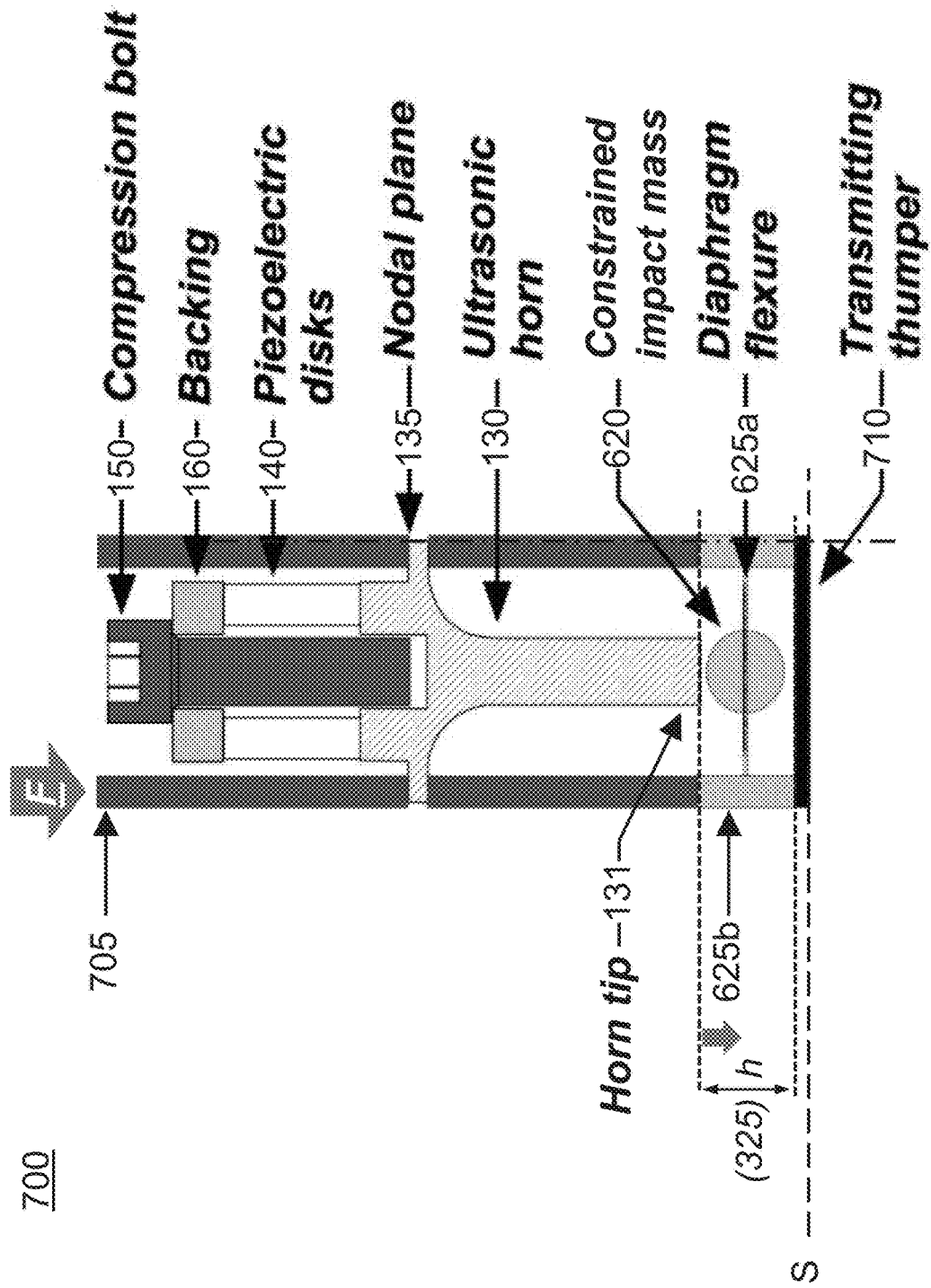
FIG. 7 shows a cross sectional view of an embodiment according to the present disclosure of the dual frequency ultrasonic and sonic transmitter including the actuator of FIG. 6A coupled to a transmitting thumper.

FIG. 7 shows a cross sectional view of an embodiment according to the present disclosure of the dual frequency ultrasonic/sonic actuator of FIG. 6A coupled to a transmitting element (710) that is a thumper. In the exemplary configuration of shown in FIG. 7, the thumper (710) replaces the longitudinal probe (110) for transmitting impact pulses at the surface S. As described above with reference to FIG. 6A, collision of the tip (131) of the horn (130) with the impact mass (620) (i.e., Newton's cradle) causes the impact mass (620) to strike a (striking surface of a) transmitter, in this case a transmitting thumper (710) that is at a fixed distance (325) from the tip (131) of the horn (130). A person skilled in the art would clearly realize that due to the flexible nature of the flexure (625a, 625b), the collision of the tip (131) of the horn (130) with the impact mass (620) may be considered an elastic collision that may be modeled according to the well-known in the art Newton's cradle. As can be seen in FIG. 7, the impact mass (620) is mounted on a diaphragm flexure (625a) that is laterally contained by an outer support wall (625b) coupled to the mounting nodal plane (135). Accordingly, ultrasonic stress to the tip is applied only via the tip (131) of the horn (130).

With continued reference to FIG. 7, according to an embodiment of the present disclosure, the impact mass (620) may be preloaded on the tip (131) of the horn (130) so that the tip (131) makes contact with the mass (620) pushing the impact mass (620) in the axial direction toward the transmitting thumper (710) while leaving a gap between the impact mass (620) and the transmitting thumper (710). Accordingly, the impact mass (710) may bounce and thus convert the ultrasonic stress impulses from the tip (131) of the horn (130) to lower frequency stress impulses (i.e., elastic waves) transmitted by the transmitting thumper (710) through the surface S. The transmitting thumper (710) consists of a membrane or thin plate and provides a path of the impacts from the contained impact mass (620) to the surface S over the large surface of the thumper (710).

With further reference to FIG. 7, a range of motion (i.e., axial displacement) of the impact mass (620) and (lower) frequency of the transmitted elastic waves are determined by properties of the diaphragm flexure (625a) and of the impact mass (620) which can be used as design parameters to generate a desired frequency. For example, a (degree of) stiffness of the diaphragm flexure (625a) may be used to control a lower resonance frequency of the combination impact mass (620) and diaphragm flexure (625a) and therefore control the lower frequency (equal to the resonance frequency) of the transmitted elastic wave. According to an embodiment of the present disclosure, the diaphragm flexure (625a) may be designed for an increased compliance normal to the plane of the diaphragm flexure (625a) (at rest) while constraining the other directions to reduce parasitic motions. In other words, as can be seen in FIG. 7, the diaphragm flexure (625a) constrains motion of the impact mass (620) into the axial direction (shown in the figure as a dashed line passing through longitudinal extension of the horn 130).

According to an embodiment of the present disclosure, the outer support wall (625b) of the diaphragm flexure (625a) is compressible so to allow a reduction in the distance (325) and therefore a reduction in the gap between the impact mass (620) and the transmitting thumper (710) for a control of a frequency of the transmitted elastic wave. As can be seen in FIG. 7, a force F applied at a mounting base (705) of the dual frequency ultrasonic/sonic actuator (700) may compress a height h of the support wall (625b) that defines the distance (325), and accordingly reduce the gap between the impact mass and the transmitting thumper. According to an exemplary embodiment of the present disclosure, the height h (i.e., the distance 325) may be controlled for a larger gap for transmission of a lower frequency (sonic) elastic wave, may be gradually controlled for a lower gap for transmission of a gradually higher frequency (sonic and ultrasonic) elastic wave, and may be controlled for no gap (thereby preventing the impact mass from bouncing) for transmission of a higher frequency ultrasonic elastic wave at a frequency equal to a frequency of the stress at the tip (131) of the horn (130). Because of the constrained nature of the impact mass (620) and axial concentration of the energy transfer from the tip (131) of the horn (130) to the transmitting thumper, a tuned (precise) frequency of the transmitted elastic wave can be obtained.

Figure 8:
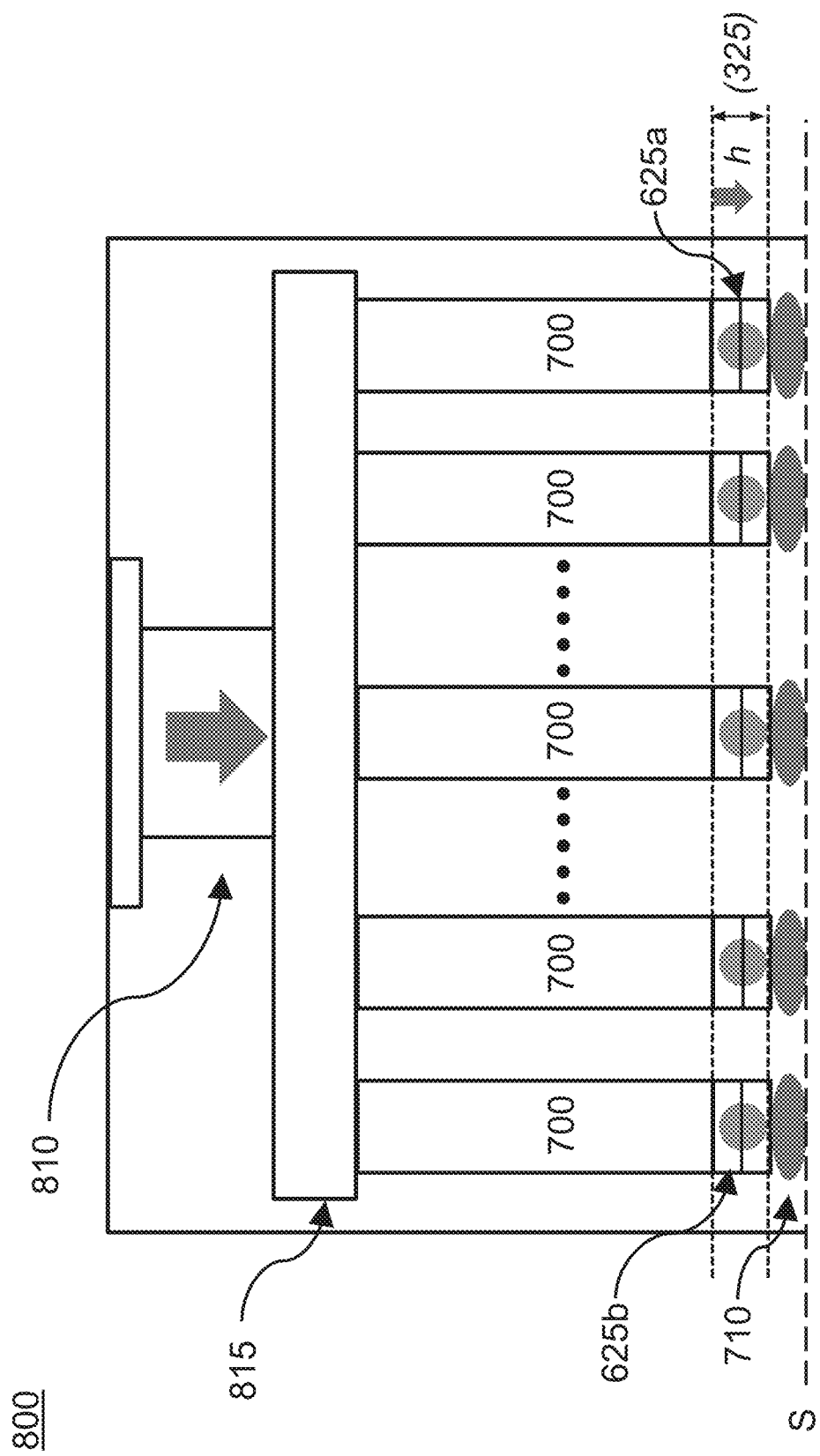
FIG. 8 shows a transmitter assembly according to an embodiment of the present disclosure that includes an array of the dual frequency ultrasonic and sonic transmitter of FIG. 7.

FIG. 8 shows an elastic wave transmitter assembly (800) according to an embodiment of the present disclosure that includes an array of a plurality of the dual frequency ultrasonic/sonic transmitters (700) of FIG. 7. According to an embodiment of the present disclosure, the plurality of the transmitters (700) may be arranged to form an effective transmitting aperture having any desired (two-dimensional) shape and not limited to the apparently aligned configuration shown in FIG. 8. A person skilled in the art would clearly understand that the effective transmitting aperture may be provided by a combined outline of the transmitting thumpers (710).

With continued reference to FIG. 8, the elastic wave transmitter (800) may include an actuator (810) that applies a force on a plate (815) that is coupled to the array of transmitters (700) so to control the height h (i.e., distance 325) of the support wall (625b), thereby controlling a frequency of an elastic wave transmitted by each of the transmitters (700) as described above with reference to FIG. 7. According to an exemplary embodiment of the present disclosure, a (degree of) stiffness of the diaphragm flexure (625a) of each of the transmitters (700) may be used to individually control a (lower) frequency of a corresponding transmitted elastic wave for a given force applied on the plate (815). In other words, a same height h resultant from an applied force on the plate (815) may result in different (lower) frequencies transmitted elastic waves from the transmitters (700). According to another embodiment of the present disclosure, the height h may be controlled to leave a gap between the impact mass (620) of each transmitter (700) and corresponding transmitting thumper (710) for transmission of lower frequency (sonic) elastic wave from the elastic wave transmitter (800). Alternatively, the height h may be controlled to leave no gap between the impact mass (620) of each transmitter (700) and corresponding transmitting thumper (710) for transmission of higher frequency (ultrasonic) elastic wave from the elastic wave transmitter (800).

With reference to FIG. 9A, according to an embodiment of the present disclosure, the transmitters (700) may be controlled (e.g., via height h=$h_1$) to transmit lower frequency elastic waves, (e.g., waves w shown in FIG. 9A having a frequency <1 KHz) that are in phase. In other words, each transmitter (700) is electrically activated at a same start time so to synchronize an emitted wave front. Accordingly, a high-pressure (low frequency, e.g., <1 KHz) combined elastic wave, W, is emitted forward by the elastic wave transmitter (800) to the traveling medium through the surface S. As it is clearly understood by a person skilled in the art, through constructive interference, the amplitude of the combined elastic wave, W, can be considerably greater than an amplitude of any of the individual elastic waves (w, from each transmitter 700) that are producing it, effectively increasing a radiated pressure level in a direction, D, of the transmission. Furthermore, because the combined elastic wave, W, is produced from a larger aperture size, it offers the generation of a collimated beam when compared to (a beam of) a wave that is generated by a single transmitter (700). As it is clearly understood by a person skilled in the art, such effect of a collimating beam is due to a divergence angle of the beam being inversely proportional to a radiating aperture size.

With reference to FIG. 9B, according to an embodiment of the present disclosure, the transmitters (700) may be controlled (e.g., via height h=$h_2$) to sequentially transmit higher frequency elastic waves, (e.g., waves w shown in FIG. 9B having a frequency >20 KHz by direct contact of the impact mass 620 to the thumper 710) by electrically activating each transmitter (700) sequentially from one end of the array (e.g., first transmitter 700 at left side of the FIG. 9B) to the other end (e.g., last transmitter 700 at right side of the FIG. 9B). In other words, each transmitter (700) is electrically activated at a different start time according to a time delay so to synchronize an angular emitted wave front. Such sequential activation of the transmitters (700) of the array of transmitters (700) causes phase differences between the emitted waves and interference that generates angular cross-sectional profile of an emitted combined elastic wave, W. Accordingly, as can be seen in FIG. 9B, effect of beam steering can be obtained, wherein an angle θ of the steered beam with respect to a direction normal to a plane of the aperture (e.g., surface 5) may be controlled by the timing of the activation sequence. It should be noted that elements depicted in FIG. 9B, as well as in FIG. 9A, are not to scale and may be exaggerated in relative dimensions for the sake of the description.

According to the above description, the elastic wave transmitter (800) according to the present teachings can generate high-power elastic waves at both high (e.g., ultrasound 20 KHz-40 KHz) and low (e.g., <1 KHz) frequencies without increasing a physical size of a corresponding transducer (e.g., 700 of FIG. 7). The disclosed transmitter (800) is a compact acoustic source of low frequency (LF) elastic waves at levels of >200 dB, comparable to a seismic air gun, while also providing the high-resolution (tens of centimeters) of high frequency (HF) ultrasound (20 KHz-40 KHz) sonar. Accordingly, such transmitter (800) may be used, for example, for exploration of ocean world sub-surfaces in which tens of kilometers sonar range is required for detecting the expected liquid ocean below, for example, Europa's ice shell, coupled with high-resolution mapping of the shallow sub-surface.

According to an exemplary embodiment of the present disclosure, elements of the piezoelectric stack (e.g., 140 of FIG. 7) of the transmitter (700) may be constructed of relaxor-ferroelectric single crystals, which can provide high electromechanical coupling factor (>0.9), allowing effective energy conversion in both transmitting and receiving energy. In other words, the transmitter (700) may also operate as a receiver (e.g., effectively a transducer) for receiving high frequency elastic waves when the gap h between the thumper (710) and the impact mass (620) is eliminated. Accordingly, received energy through the thumper (710) may be coupled to the piezoelectric stack (140) and a corresponding electrical signal detected may indicate an amplitude/power and frequency of a received high frequency elastic wave. Furthermore, use of such relaxor-ferroelectric single crystals can provide broad bandwidth and high sensitivity of the transducer (700) response even at cryogenic temperatures. Accordingly, the transducer (e.g., 700) according to the present teachings may be used in various missions to cold bodies in the solar system, where there is a need for analysis of the icy sub-surface geology, including the layered structure, elastic properties, and possible presence of interstitial liquids or voids.

A number of embodiments of the disclosure have been described. Nevertheless, it will be understood that various modifications may be made without departing from the spirit and scope of the present disclosure. Accordingly, other embodiments are within the scope of the following claims.

The examples set forth above are provided to those of ordinary skill in the art as a complete disclosure and description of how to make and use the embodiments of the disclosure and are not intended to limit the scope of what the inventor/inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The invention claimed is:

1. A dual frequency actuator, comprising:
    an ultrasonic actuator comprising a horn coupled to a source of ultrasonic frequency vibrations, the horn configured to amplify the ultrasonic frequency vibrations along an axial direction of the horn;
    a transmitting element at a substantially fixed distance from the horn, the transmitting element flexibly coupled through a diaphragm flexure that is laterally constrained by an outer support wall rigidly coupled to the horn; and
    an impact mass disposed between the horn and the transmitting element, a displacement of the impact mass being constrained into the axial direction,
    wherein the impact mass is configured to strike the transmitting element in response to the ultrasonic frequency vibrations to produce sonic impacts at the transmitting element.

2. The dual frequency actuator according to claim 1, wherein the displacement of the impact mass is constrained by an additional flexure that is coupled to the impact mass.

3. The dual frequency actuator according to claim 2, wherein:
    the transmitting element comprises a striking surface that is flexibly coupled through the diaphragm flexure, and
    the impact mass strikes the striking surface that is positioned at a distance from the impact mass.

4. The dual frequency actuator according to claim 3, wherein the additional flexure comprises an additional diaphragm flexure that is laterally constrained by an additional outer support wall.

5. The dual frequency actuator according to claim 4, wherein the additional outer support wall of the additional flexure is rigidly coupled to the outer support wall of the diaphragm flexure.

6. The dual frequency actuator according to claim 5, wherein the outer support wall of the additional flexure is rigidly coupled to a nodal plane of the horn to decouple the ultrasonic frequency vibrations from the transmitting element.

7. The dual frequency actuator according to claim 5, wherein the outer support wall of the additional flexure is rigidly coupled to a tip of the horn to couple the ultrasonic frequency vibrations to the transmitting element.

8. The dual frequency actuator according to claim 2, wherein the dual frequency actuator comprises a bore that forms a hollow core along the axial direction for insertion of a tube that extends from the transmitting element to a base of the dual frequency actuator and passes through the impact mass.

9. The dual frequency actuator according to claim 8, wherein the tube further constrains the impact mass into the axial direction.

10. The dual frequency actuator according to claim 8, wherein the transmitting element is a drill bit configured to impact a contact surface that is in contact with a tip of the drill bit.

11. The dual frequency actuator according to claim 2, wherein:
    the additional flexure comprises a diaphragm flexure that is laterally constrained by an additional outer support wall, and
    the transmitting element is a thumper.

12. The dual frequency actuator according to claim 11, wherein the additional outer support wall is compressible so to allow adjustment of a distance between a tip of the horn and the impact mass in a range from a gap to no gap.

13. A transmitter comprising:
    a plurality of dual frequency actuators according to claim 12 arranged as an array; and
    an actuator configured to exert a force onto the array to adjust, for each of the plurality of the dual frequency actuators, a distance between a tip of the horn and the impact mass,
    wherein the transmitter is configured to operate according to at least two modes of operation:
        i) a low frequency sonic transmitter mode wherein a distance between the tip of the horn and the impact mass of each dual frequency actuator of the array is non-zero, and
        ii) a high frequency ultrasonic transmitter mode wherein a distance between the tip of the horn and the impact mass of each dual frequency actuator of the array is zero.

14. The transmitter according to claim 13, wherein for operation in the low frequency sonic transmitter mode, each of the plurality of dual frequency actuators is electrically activated at a same start time so to synchronize an emitted wave front.

15. The transmitter according to claim 13, wherein for operation in the high frequency ultrasonic transmitter mode, each of the plurality of dual frequency actuators is electrically activated sequentially according to an order of each of said actuators in the array, so to generate a high-resolution angular cross-sectional profile of an emitted combined wave.

16. A method for generation of dual ultrasonic and sonic frequency impacts, the method comprising:
    coupling ultrasonic frequency vibrations to a horn for amplifying the ultrasonic frequency vibrations along an axial direction of the horn;
    arranging a transmitting element at a substantially fixed distance from the horn, the transmitting element flexibly coupled through a diaphragm flexure that is laterally constrained by an outer support wall rigidly coupled to the horn;
    arranging an impact mass between the horn and the transmitting element, a displacement of the impact mass being constrained into the axial direction; and
    striking, via the impact mass, the transmitting element in response to the ultrasonic frequency vibrations to produce sonic impacts at the transmitting element.

17. The method according to claim 16, further comprising:
    rigidly coupling the transmitting element to the horn to produce ultrasonic impacts at the transmitting element.

* * * * *